US009005290B2

(12) United States Patent
Morrison, III

(10) Patent No.: US 9,005,290 B2
(45) Date of Patent: Apr. 14, 2015

(54) SPINAL INTERBODY DEVICE

(75) Inventor: Thomas J. Morrison, III, Atlanta, GA (US)

(73) Assignee: Medgem LLC, Atlanta, GA (US)

( * ) Notice: Subject to any disclaimer, the term of this patent is extended or adjusted under 35 U.S.C. 154(b) by 1446 days.

(21) Appl. No.: 12/134,946

(22) Filed: Jun. 6, 2008

(65) Prior Publication Data
US 2008/0306599 A1  Dec. 11, 2008

Related U.S. Application Data

(60) Provisional application No. 60/942,802, filed on Jun. 8, 2007.

(51) Int. Cl.
*A61F 2/44* (2006.01)
*A61F 2/46* (2006.01)
*A61F 2/30* (2006.01)

(52) U.S. Cl.
CPC ............. *A61F 2/442* (2013.01); *A61F 2/30965* (2013.01); *A61F 2/4455* (2013.01); *A61F 2/4611* (2013.01); *A61F 2002/30014* (2013.01); *A61F 2002/30242* (2013.01); *A61F 2002/30245* (2013.01); *A61F 2002/3025* (2013.01); *A61F 2002/30448* (2013.01); *A61F 2002/30563* (2013.01); *A61F 2002/30565* (2013.01); *A61F 2002/30616* (2013.01); *A61F 2002/444* (2013.01); *A61F 2220/005* (2013.01); *A61F 2230/0071* (2013.01); *A61F 2250/0018* (2013.01); *A61F 2310/00017* (2013.01); *A61F 2310/00023* (2013.01); *A61F 2310/00029* (2013.01)

(58) Field of Classification Search
USPC ........... 623/17.11, 17.12, 17.13, 17.14, 17.16
See application file for complete search history.

(56) References Cited

U.S. PATENT DOCUMENTS

| 5,534,028 | A | 7/1996 | Bao et al. |
| 5,865,846 | A | 2/1999 | Bryan et al. |
| 6,348,071 | B1 | 2/2002 | Steffee et al. |
| 6,419,704 | B1 | 7/2002 | Ferree |
| 6,533,818 | B1 * | 3/2003 | Weber et al. ............... 623/17.16 |
| 6,582,468 | B1 | 6/2003 | Gauchet |
| 6,607,558 | B2 * | 8/2003 | Kuras .......................... 623/17.16 |
| 7,025,787 | B2 | 4/2006 | Bryan et al. |
| 2003/0220691 | A1 | 11/2003 | Songer et al. |
| 2004/0010316 | A1 | 1/2004 | William et al. |

(Continued)

FOREIGN PATENT DOCUMENTS

| DE | 4423826 A1 | 1/1995 |
| WO | 02087480 A1 | 11/2002 |

(Continued)

OTHER PUBLICATIONS

"Medtronic Sofamor Danek 510(k): SATELLITE Spinal System," Aug. 2005, Department of Health & Human Services, Food and Drug Administration, Rockville, MD.

*Primary Examiner* — Christian Sevilla
(74) *Attorney, Agent, or Firm* — Hunton & Williams, LLP

(57) ABSTRACT

A multi-material spinal interbody device includes an inner dampener of compressible material in combination with a rigid outer material. The rigidity of the outer periphery of curved surfaces of the device, such as in an eluipsoid shape, provide support as a replacement to the nucleus propulsus, with the inner dampener providing for absorption of spinal forces.

23 Claims, 4 Drawing Sheets

(56) References Cited

U.S. PATENT DOCUMENTS

| | | | |
|---|---|---|---|
| 2004/0030391 A1* | 2/2004 | Ferree | 623/17.16 |
| 2004/0054411 A1* | 3/2004 | Kelly et al. | 623/17.13 |
| 2004/0106995 A1* | 6/2004 | Le Couedic et al. | 623/17.11 |
| 2004/0186576 A1* | 9/2004 | Biscup et al. | 623/17.12 |
| 2005/0085909 A1 | 4/2005 | Eisermann | |
| 2005/0165485 A1* | 7/2005 | Trieu | 623/17.13 |
| 2006/0235528 A1* | 10/2006 | Buettner-Janz | 623/17.14 |
| 2007/0088441 A1 | 4/2007 | Duggal et al. | |
| 2009/0069894 A1* | 3/2009 | Duggal et al. | 623/17.16 |

FOREIGN PATENT DOCUMENTS

| | | | |
|---|---|---|---|
| WO | 03003952 A1 | 1/2003 | |
| WO | 03094806 A1 | 11/2003 | |
| WO | WO 2006114646 A1 * | 11/2006 | A61B 17/16 |
| WO | 2007084823 A2 | 7/2007 | |

* cited by examiner

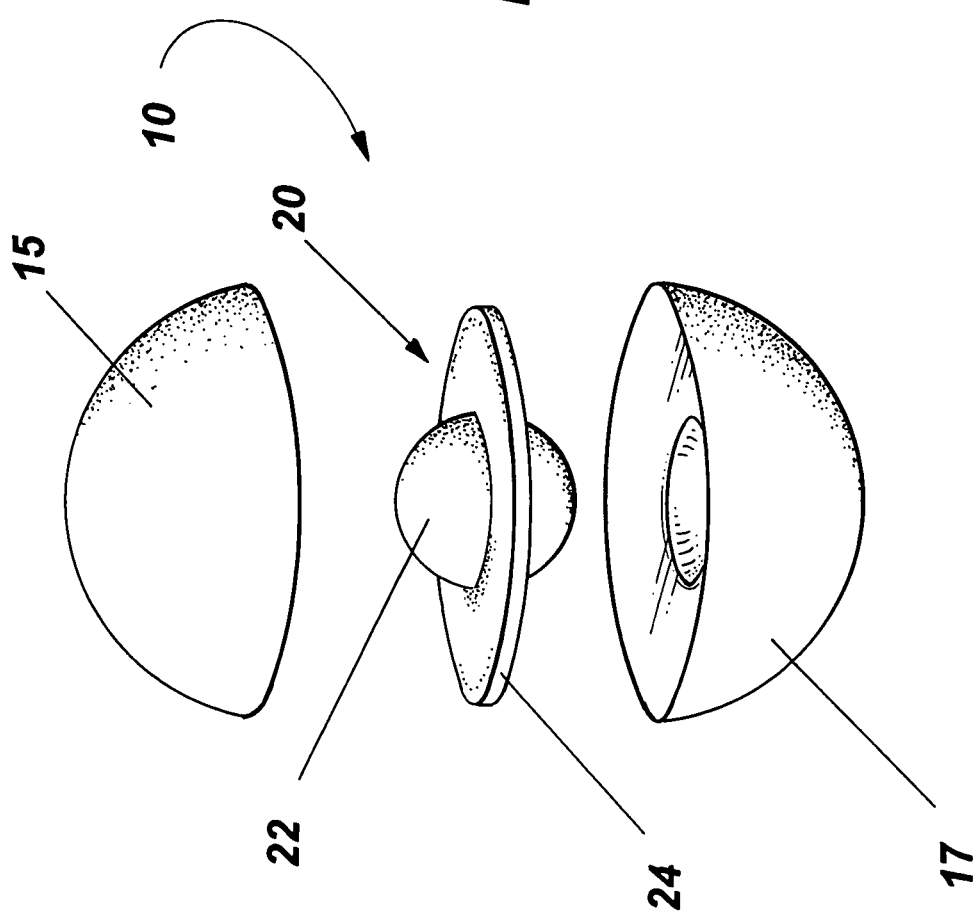

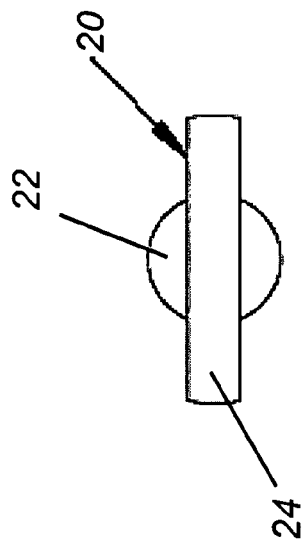
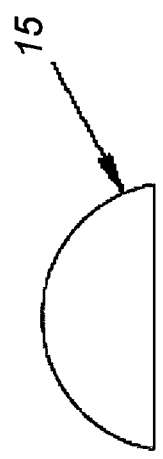
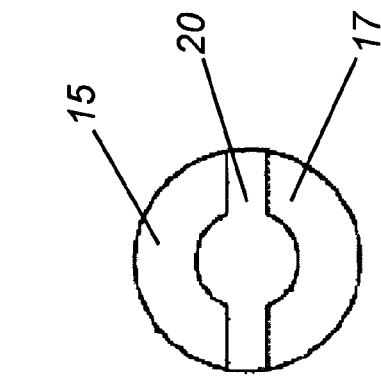
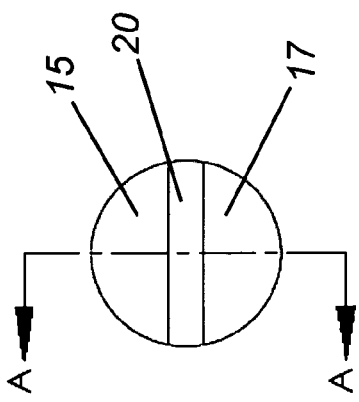
FIG. 3
FIG. 5
FIG. 2
FIG. 4

SPINAL INTERBODY DEVICE

CROSS-REFERENCE TO RELATED APPLICATIONS

This application claims priority to patent application Ser. No. 60/942,802 filed Jun. 8, 2007, which is relied on and incorporated by reference.

BACKGROUND OF THE INVENTION

The present invention relates to fusion and non-fusion spinal interbody devices.

Spinal interbody devices such as the Fernstrom ball developed by Dr. Ulf Fernstrom, the Harmon Spinal Sphere of the Austenal Company (New York, N.Y.) and the more recent Satellite Spinal System of Medtronic Sofamar Danek (Memphis, Tenn.) have attempted stabilization in a disc interspace with an insertable solid sphere. Because of the rigidity and lack of compression of such solid spheres, undesirable subsidence of the device may result leading to possible nerve agitation and further corrective surgery.

Nucleus propulsus replacement has also been attempted with non-rigid hydrogels, such as disclosed in U.S. Pat. No. 7,214,245 to Marcolongo et al. Such hydrogels, however, are prone to migration and escape from the interbody space.

Accordingly, a need exists for a compressible spinal interbody device that avoids the problems of interbody devices that are either too rigid or too yielding.

SUMMARY OF THE INVENTION

In embodiments, the present invention answers this need by providing an interbody device with both rigid and compressible components for both supporting and absorbing axial loads while limiting subsidence and endplate erosion. The compressible components include material of greater compressibility than material of rigid components.

In one embodiment, rigid material may include, but not limited to, biocompatible materials such as polyetheretherketone (PEEK), titanium, stainless steel and cobalt chromium alone or in combination with other materials. In further embodiments, the compressible material may include, but not limited to, biocompatible materials such as elastomers, ultra high molecular weight polyethylene (UHMWPE), polycarbonate urethane (Sulene-PCU), polyethylene terephtalate (Sulene_PET), hydrogels (including with a polyethylene jacket), polyvinyl alcohol hydrogel (Aquarelle) and polycarbonate urethane elastomer (Newcleus) alone or in combination with other materials.

In embodiments of the invention, an interbody device includes top and bottom shells of a first material and an inner dampener of second dampening material. In some embodiments a plurality of shell components, such as quadrant shell pieces may be coupled with an inner dampener material. In one embodiment, the interbody device may be formed by a plurality of rigid material pieces interspersed with compressible material.

In alternative embodiments, an inner dampener may comprise a mechanical spring and like compressible components of various materials.

In one embodiment, an interbody device of the invention may be an ellipsoid, including but not limited to a sphere, oblate spheroid, prolate spheroid and scalene ellipsoids. In other embodiments of the invention an interbody device may compromise a partial ellipsoid, partial polyhedrons and other shapes configured to include top and bottom curved surface portions for contacting vertebral bodies.

In some embodiments, an interbody device includes an inner dampener having an ellipsoidal compressible core portion and a compressible equatorial planar surface portion extending outwardly from the core. In further embodiments the inner dampener includes an ellipsoidal compressible core portion and a compressible equatorial planar surface portion extending outwardly from the core.

In embodiments of the invention, compressible and rigid materials may be combined through coupling means including, but not limited to, overmolding (including injection molding), press-fitting, adhesives, mechanical fastening and the like.

In embodiments of the invention, an interbody device of the present invention may be adapted for interbody fusion procedures to provide improved stabilization, stress-shielding and maintenance of placement in the interbody space. In other embodiments of the present invention an interbody device of the present invention may be adapted for interbody non-fusion procedures to provide dynamic stabilization, stress-shielding, reduced movement, reduced likelihood of escape and reduced subsidence.

BRIEF DESCRIPTION OF THE DRAWINGS

FIG. 1 is an exploded perspective view of a multi-component spherical interbody device in one embodiment of the present invention.

FIG. 2 is a basic plan view of a top outer shell component of a spherical interbody device in one embodiment of the present invention.

FIG. 3 is a basic plan view of an inner dampener component of a spherical interbody device in one embodiment of the present invention.

FIG. 4 is a basic plan view of a spherical interbody device in one embodiment of the present invention.

FIG. 5 is a cross-sectional plan view along Section A-A of FIG. 4 in one embodiment of the present invention.

DESCRIPTION OF THE INVENTION

Figure 7:
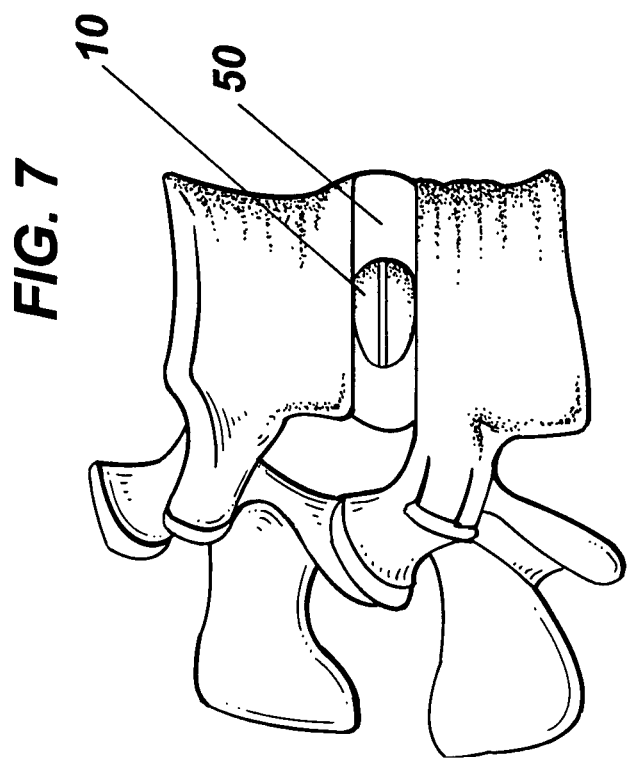
FIG. 7 is a front perspective view of a multi-component non-spherical ellipsoid interbody device depicted in the intervertebral space in one embodiment of the present invention.

The present invention provides an apparatus for disc nucleus replacement to promote the support and absorption of axial loads while limiting subsidence and endplate erosion in both vertebral fusion and non-fusion spinal treatments. In non-fusion embodiments, the combination of rigid and compressible components with curved surface portions adapted for placement and contacting the vertebral bodies may further promote motion preservation and dynamic stabilization.

Although a spinal interbody device of the present invention is described herein in ellipsoid embodiments, including spheres and spheroids, it will be appreciated that various shapes including curved surface portions may be provided in other embodiments.

Referring to FIGS. 1-5, an interbody device 10 in one embodiment of the invention is a spherical shape. The device 10 includes a top outer shell 15, a bottom outer shell 17 and an inner dampener 20. The outer shells 15 and 17 may comprise sphere portions adapted to couple to inner dampener 20. In some embodiments the top outer shell 15 and bottom outer shell 17 may be identical in size and shape. In other embodiments the shells 15 and 17 may be differently size or shaped. The outer shells may comprise relatively rigid biocompatible materials, including, but not limited to, PEEK or carbon fiber reinforced PEEK, titanium, stainless steel, cobalt chromium and the like, either alone or in combination with these or other materials.

The inner dampener 20 in one embodiment includes a dampener core 22. The dampener core may be provided in ellipsoidal or other shapes adapted for compressibility. In some embodiments, the inner dampener comprises a dampener core 22 and a planar equatorial projection 24 extending outward from dampener core 22. The inner dampener 20 may comprise compressible material including, but not limited to, polyethylene, polycarbonate urethane (Sulene), polyethylene terephtalate (Sulene), HP-100 silicone elastomer, hydrogel with a polyethylene jacket, polyvinyl alcohol hydrogel (Aquarelle), polycarbonate urethane elastomer (Newcleus) or other elastomers, polymers or rubber-like substances, either alone or in combination with these or other materials.

With particular reference to FIG. 1, in one embodiment of the invention the outer shells 15 and 17 may include a concave inner portion adapted for coupling to an ellipsoid-shaped, including spherical, dampener core 22 of the inner dampener 20. The dampener equatorial planar projection 24 extends outward between the non-concave periphery portions of the outer shells 15 and 17.

With further reference to FIGS. 2-5, in embodiments the interbody device 10 may have diameters of various sizes, including ranging from about 6 to about 18 mm, although such sizes may be adapted to the particular patient or purpose. In one embodiment, the interbody devices has a spherical diameter of about 11 mm. In such embodiment, the inner dampener core 22 has a spherical diameter of about 5 mm and each of the outer shells 15 and 17 have a radius measure to the inner dampener core 22 of about 3 mm. In such embodiment the inner dampener equatorial planar projection 25 has a thickness of about 2 mm. In some embodiments of the invention, a kit may be provide including a range of sizes and/or shapes of the interbody device 10.

Figure 6:
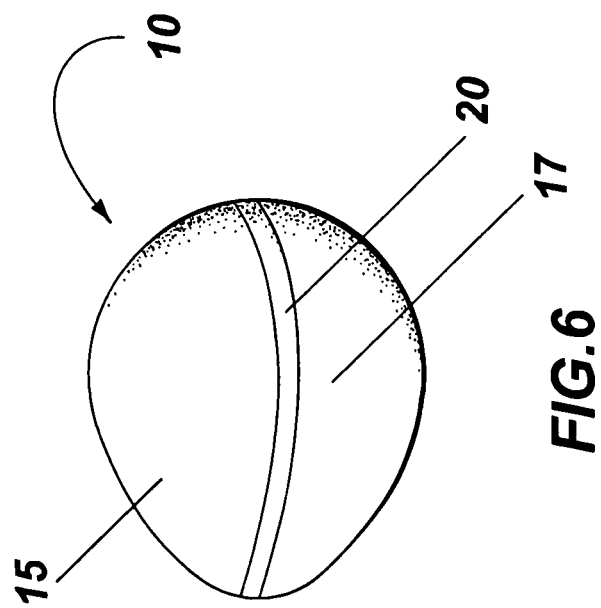
FIG. 6 is a front perspective view of a multi-component non-spherical ellipsoid interbody device in one embodiment of the present invention.

FIG. 6 shows a non-limiting alternative embodiment in which the interbody device 10 is provided in a non-spherical ellipsoid shape, such as an oblate spheroid or egg/ovular shape with a larger equatorial diameter and height. In other embodiments of the invention, prolate spheroids and scalene ellipsoid shapes may adapted for use in the present invention.

With further reference to FIG. 7, an interbody device 10 is shown implanted in an annular disc 50 with top and bottom curved surface portions abutting the vertebral bodies. The interbody device 10 may move within the biconvexity of the endplates of the adjacent vertebral bodies and the inner dampener 20 also allows for axial compression. In embodiments of the invention, the interbody device 10 migrates near the internal axis of rotation and becomes a substitute for the nucleus propulsus.

Figure 8:
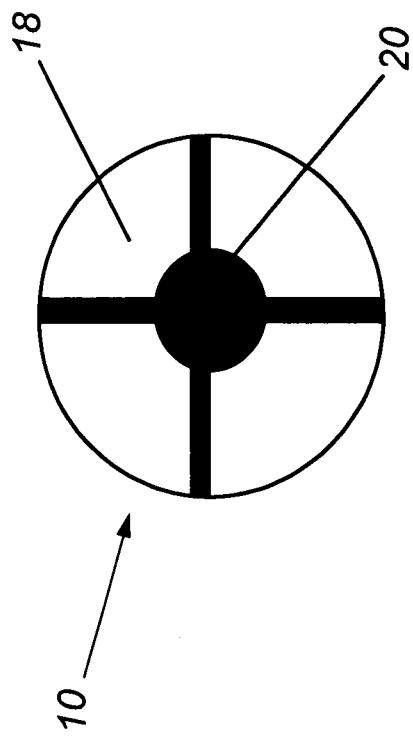
FIG. 8 is a basic cross-section plan view of a top plan view of a an interbody device including outer shell quadrants and an inner damper in one embodiment of the present invention.

With reference to FIG. 8, in another embodiment of the invention the interbody device 10 may comprise a plurality of outer shells, such as outer shell quadrants 18 to provide a larger inner dampener 20. As shown in the embodiment depicted in FIG. 8, a plurality of equatorial planar projections may also be provided.

In other embodiments of the present invention, an inner dampener material may be interspersed or molded with rigid materials to also achieve the advantages of sufficient interbody support with compressibility.

In various embodiments of the present invention an interbody device 10 may be constructed as one piece or assembled as a unit. In some embodiments of the invention, overmolding processes, including but not limited to injection and/or insert molding, may be used to couple an inner dampener 20 and outer shell materials. In other embodiments, press-fitting, adhesives, mechanical fastening and like coupling means may be used. In alternative embodiments, a mechanical spring or similarly compressible apparatus may be provided in place of or complimentary to an inner dampener 20 or compressible material.

In one embodiment, outer shells 15 and 17 may be molded and include PEEK and the shells inserted at room temperature into a second mold. The second mold holds the two PEEK-containing outer shell parts interstitially and a damper material or materials, such as but not limited to elastomers, UHMW PE and the like, are inserted into the cavity between the outer shells. The molten damper material adheres at the molecular level with the PEEK during such process. In one embodiment, the inner cavity space between the PEEK outer shell parts may includes a torturous path within the inner cavity so that when the damper material is inserted in liquid form, it will flow into the paths, solidify and then become strongly bonded.

In one embodiment, surgically implanting the interbody device 10 could occur from a posterior approach. The device 10 may be implanted using a TLIF (transforaminal lumbar interbody fusion) or unilateral PLIF (posterior lumbar interbody fusion) technique that is common for surgeons performing fusions with interbody devices today. The interbody device 10 would also have the ability to be implanted in an ALIF or XLIF approach. In other embodiments, microdiscectomy, hemilaminectomy or laminotomy techniques may also be used. In the posterior approach, instead of removing as much disc as possible and performing an arthrodesis, enough disc is removed to place the device slightly posterior and midline in the intervertebral space and have the outer shells or curved surfaces of the device 10 rest on the endplates of the vertebral bodies.

Figure 9:
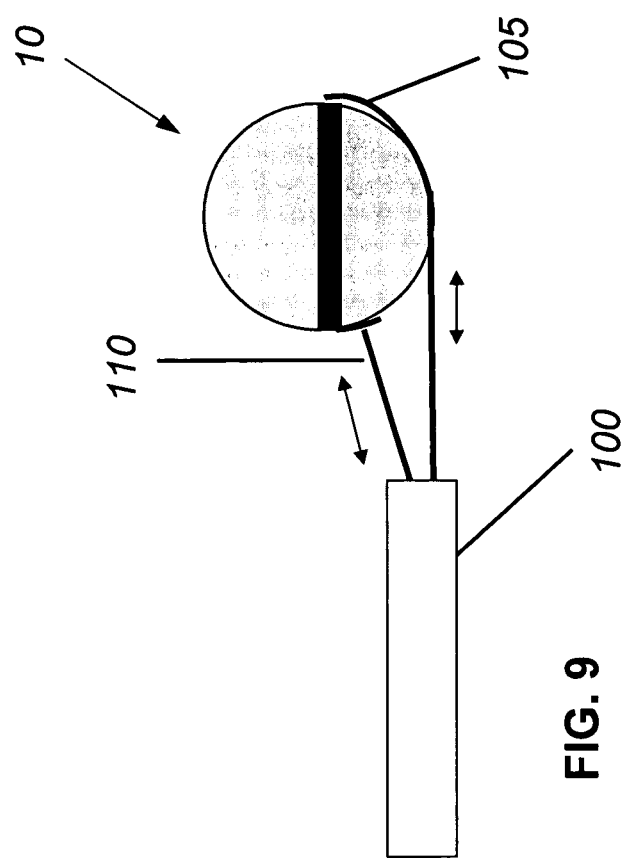
FIG. 9 is a basic schematic view of a retracting grasper apparatus and interbody device in one embodiment of the present invention.

Referring to FIG. 9, in one embodiment an interbody device grasping and positioning tool 100 may be provided for implanting the interbody device 10. Such tool may include a first arm 105 with curved contour to the shape of the interbody device 10. An opposite arm 110 may be provided for also supporting the device 10. In such embodiments, the curved grasping arm 105 permits positioning of the interbody device 10 with reduced risk of interfering with nerves or similar undesirable surgical contact of other positioning tools. One or both arms 105 and 110 may be retractable when the interbody device 10 is properly positioned. In alternative embodiments, arms 105 and 110 may be replaced by other retractable means, such as a partial scoop-shaped element contoured to the interbody device 10 and the like. In certain embodiment a grasping/positioning tool may be provided in a kit with one or more interbody devices 10, including both grasping/positioning tools and interbody devices 10 of various sizes and shapes.

While the invention has been described with reference to structures and methods in some embodiments of the invention, the invention is not intended to be limited thereto, but extends to modifications and improvements with the scope or equivalence of the claims.

What is claimed is:

1. An interbody device comprising a first curved and centrally convex vertebral body contact surface of a top shell, a second curved and centrally convex lower vertebral body contact surface of a bottom shell opposite the first vertebral body contact surface and a compressible inner dampener with an ellipsoid central core portion coupled between concave, ellipsoidal inner surface portions underlying each of the centrally convex vertebral body contact surfaces of the top and bottom shells and a compressible equatorial planar surface portion extending outwardly from around a circumference of an equatorial region of the central core portion and between non-concave periphery portions of the top and bottom shells.

2. The interbody device of claim 1, wherein said inner dampener includes at least one material of a greater compressibility than one or more materials in the first and second vertebral body contact surfaces.

3. The interbody device of claim 2, wherein the device further comprises an ellipsoidal shape.

4. The interbody device of claim 3, wherein said ellipsoidal shape of the device is selected from the group consisting of an oblate spheroid, prolate spheroid and scalene ellipsoid.

5. The interbody device of claim 3, wherein said ellipsoidal shape of the device is a sphere.

6. The interbody device of claim 2, wherein the inner surface portions underlying each of the first and second curved vertebral body contact surfaces include polyetheretherketone molded to the at least one material of the inner dampener having greater compressibility than polyetheretherketone.

7. The interbody device of claim 3, wherein the inner surface portions underlying each of the first and second curved vertebral body contact surfaces include polyetheretherketone molded to the at least one material of the inner dampener having greater compressibility than polyetheretherketone.

8. The interbody device of claim 7, wherein the top shell comprises a partial ellipsoid outer surface portion including the first curved vertebral body contact surface and the bottom shell comprises a partial ellipsoid outer surface portion including the second curved vertebral body contact surface, and wherein the top and bottom shells are separated by and joined as a unitary device with the inner dampener.

9. The interbody device of claim 1, wherein the top shell comprises a partial ellipsoid outer surface portion including the first curved vertebral body contact surface and the bottom shell comprises a partial ellipsoid outer surface portion including the second curved vertebral body contact surface, and wherein the top and bottom shells are separated by and joined as a unitary device with the inner dampener.

10. The interbody device of claim 4, wherein the top shell comprises a partial ellipsoid outer surface portion including the first curved vertebral body contact surface and the bottom shell comprises a partial ellipsoid outer surface portion including the second curved vertebral body contact surface, and wherein the top and bottom shells are separated by and joined as a unitary device with the inner dampener.

11. An interbody device comprising two or more materials of different compressibility in an ellipsoidal shape having at least opposite curved and centrally convex surfaces in opposite outer shell portions adapted for contacting vertebral bodies wherein an inner dampener is coupled between the opposite outer shell portions and the inner dampener includes a compressible central core portion with top and bottom convex surfaces secured within central recessed portions of each shell underlying the centrally convex surfaces of the opposite outer shell portions and a compressible planar surface portion extending outwardly from around a perimeter around the central core portion and between non-concave periphery portions of each shell.

12. The interbody device of claim 11, comprising two or more outer shells including a first resilient material and an inner dampener of a second compressible material.

13. The interbody device of claim 12, wherein the first resilient material is polyetheretherketone and the second compressible material is an elastomer.

14. The interbody device of claim 12, wherein the first resilient material is polyetheretherketone and the second compressible material is polyethylene.

15. The interbody device of claim 11, wherein the ellipsoidal shape is a sphere.

16. The interbody device of claim 11, wherein said ellipsoidal shape is selected from the group consisting of an oblate spheroid, prolate spheroid and scalene ellipsoid.

17. The interbody device of claim 13, wherein the ellipsoidal shape is a sphere.

18. The interbody device of claim 13, wherein said ellipsoidal shape is selected from the group consisting of an oblate spheroid, prolate spheroid and scalene ellipsoid.

19. The interbody device of claim 2, wherein the inner dampener includes an elastomer and the first and second vertebral body contact surfaces each include at least one of polyetheretherketone, titanium, stainless steel and cobalt chromium.

20. The interbody device of claim 11, wherein the central core portion of the inner dampener is an ellipsoidal shape selected from the group consisting of an oblate spheroid, prolate spheroid and scalene ellipsoid.

21. The interbody device of claim 20, wherein the compressible planar surface of the inner dampener extends outward from an equatorial region of the central core of the inner dampener.

22. The interbody device of claim 16, wherein the central core portion of the inner dampener is an ellipsoidal shape selected from the group consisting of an oblate spheroid, prolate spheroid and scalene ellipsoid.

23. The interbody device of claim 22, wherein the compressible planar surface of the inner dampener extends outward from an equatorial region of the central core portion of the inner dampener.

* * * * *